United States Patent
Chakravarthy et al.

(10) Patent No.: US 11,948,684 B2
(45) Date of Patent: Apr. 2, 2024

(54) DIAGNOSTIC PROCESS FOR DISEASE DETECTION USING GENE EXPRESSION BASED MULTI LAYER PCA CLASSIFIER

(71) Applicants: Latha Chakravarthy, Beavercreek, OH (US); Prathik Abhay Chakravarthy, Beavercreek, OH (US); Sudarshan Venkat Chakravarthy, Beavercreek, OH (US); Vasu Devan Chakravarthy, Beavercreek, OH (US)

(72) Inventors: Latha Chakravarthy, Beavercreek, OH (US); Prathik Abhay Chakravarthy, Beavercreek, OH (US); Sudarshan Venkat Chakravarthy, Beavercreek, OH (US); Vasu Devan Chakravarthy, Beavercreek, OH (US)

(*) Notice: Subject to any disclaimer, the term of this patent is extended or adjusted under 35 U.S.C. 154(b) by 805 days.

(21) Appl. No.: 16/888,722

(22) Filed: May 30, 2020

(65) Prior Publication Data
US 2020/0402660 A1 Dec. 24, 2020

Related U.S. Application Data

(60) Provisional application No. 62/921,478, filed on Jun. 20, 2019.

(51) Int. Cl.
*G16H 50/20* (2018.01)
*G16B 25/10* (2019.01)
(Continued)

(52) U.S. Cl.
CPC ............. *G16H 50/20* (2018.01); *G16B 25/10* (2019.02); *G16H 10/40* (2018.01); *G16H 10/60* (2018.01);
(Continued)

(58) Field of Classification Search
None
See application file for complete search history.

(56) References Cited

U.S. PATENT DOCUMENTS

| | | | |
|---|---|---|---|
| 2012/0157336 A1* | 6/2012 | Keller | G16B 25/00 435/6.12 |
| 2013/0023434 A1* | 1/2013 | Van Laar | G16B 40/20 702/19 |

(Continued)

OTHER PUBLICATIONS

Liu, JX., Wang, YT., Zheng, CH. et al. Robust PCA based method for discovering differentially expressed genes. BMC Bioinformatics 14 (Suppl 8), S3 (2013). https://doi.org/10.1186/1471-2105-14-S8-S3 (Year: 2013).*

*Primary Examiner* — Devin C Hein

(57) ABSTRACT

A diagnostic process for disease detection using gene expression based PCA (Principal Component Analysis) classifier is provided. The present invention includes a method of diagnosing disease in a patient by performing a multilayer PCA classification that analyzes gene expression profiles of patients' biological samples to predict their class as disease or healthy, uses patients' biological samples to extract a set of fingerprint genes for specific disease and cell type which can be used as identification features, and classifies patient biological samples as disease or healthy based on differential gene expression profiles of the fingerprint genes. The present invention also implements the multilayer PCA classifier on patients' biological samples to extract a set of fingerprint genes for specific disease and cell type, and tabulates the fingerprint gene information in a database that will be referenced for disease diagnosis, prescreening in early stages of disease, and for confirming the stage of the disease, executed through the many embodiments of the invention.

6 Claims, 11 Drawing Sheets

(51) Int. Cl.
*G16H 10/40* (2018.01)
*G16H 10/60* (2018.01)
*G16H 50/30* (2018.01)
*G16H 50/50* (2018.01)
*G16H 50/70* (2018.01)
*G16H 70/60* (2018.01)

(52) U.S. Cl.
CPC ............. *G16H 50/30* (2018.01); *G16H 50/50* (2018.01); *G16H 50/70* (2018.01); *G16H 70/60* (2018.01)

(56) References Cited

U.S. PATENT DOCUMENTS

| | | | | |
|---|---|---|---|---|
| 2015/0356242 A1* | 12/2015 | George | ................ | G16B 25/10 |
| | | | | 702/19 |
| 2016/0068915 A1* | 3/2016 | Kennedy | ................ | G16B 25/10 |
| | | | | 435/6.12 |
| 2018/0357379 A1* | 12/2018 | Koh | ................ | G16B 40/00 |
| 2020/0199671 A1* | 6/2020 | Pan | ................ | G16B 40/00 |

\* cited by examiner

DIAGNOSTIC PROCESS FOR DISEASE DETECTION USING GENE EXPRESSION BASED MULTI LAYER PCA CLASSIFIER

CROSS-REFERENCE TO RELATED APPLICATION

This application claims the benefit of priority of U.S. provisional application No. 62/921,478, filed Jun. 20, 2019, the contents of which are herein incorporated by reference.

BACKGROUND OF THE INVENTION

The present invention relates to a diagnostic process for disease detection using gene expression based Principal Component Analysis (PCA) classifier.

Accurate diagnosis and early screening of several diseases helps administer prompt therapy and timely treatment which not only saves lives, but also improves the quality of life. Diagnosis of several diseases such as cancers, specifically leukemia and its differentiation from and classification into its various subtypes is achieved through light microscopy and flow cytometry to help identify key morphologic features. However, the process becomes challenging in the absence of these specific features, thus affecting classification of certain cancers into their subtypes, which could otherwise provide useful clinical and prognostic information. On the other hand, diagnosis of diseases such as Autism Spectrum Disorder is still prevalently based on behavioral symptoms. Determining the gene expression regulation may be important for understanding the pathological basis of autism and help uncover the underlying basis of the disorder. Further, early screening of several neurodegenerative diseases such as Alzheimers, Parkinsons, and Huntingtons, enables prompt treatment options leading to better prognosis and quality of life. Analyzing the disease on a genetic level by leveraging from the difference in expression profile of disease verses unaffected controls can be used to discriminate between them based on their genetic signatures. By identifying key genetic variations across several cell types especially those cell types that are easily available such as blood cells (as opposed to tissues/cells in internal organs, brain), will help identify the neurodegeneration/disease at an earlier stage. This necessitates the need for a technique that can efficiently detect and diagnose disease across several cell/tissue types on a genetic level.

Machine learning (ML) is a branch of artificial intelligence (AI) where systems can learn from data, identify patterns, and make decisions with minimal human intervention. The main objective of ML techniques is to produce a model which can be used to perform classification, prediction, or estimation. Classification algorithms use ML to analyze data samples and predict their class. With the advent of new technology, for example microarray—a high throughput genomic technology that measures the expression of thousands of genes simultaneously, large amount of genetic data are available for medical research. Classification algorithms leverage from the difference in expression profile of disease vs. unaffected controls and can be used to discriminate between them based on their genetic signatures. Currently, the classifiers, and machine learning techniques in general, are limited in their performance due to the high dimensionality of the gene expression data, or the feature space. Since thousands of genes' expression profiles are measured by microarrays, it could cause data overfitting especially when the sample size of the patients is very small. As can be seen, there is a need for extracting a smaller subset comprising of the most essential features (genes) that not only provides sufficient information that can help discriminate between disease and healthy subjects, but which can also reduce computational burden, as well as aid in a better understanding of the biological aspects of the disease.

SUMMARY OF THE INVENTION

In one aspect of the present invention, a method of diagnosing disease in a patient comprises: performing a multilayer PCA classification that analyses gene expression profiles of patients' biological samples and predicts their class as disease or healthy; using patients' biological samples to extract a set of fingerprint feature genes for specific disease and cell type which can be used as identification features for the specific disease and cell type; classifying patient biological samples as disease or healthy based on differential gene expression profiles of the fingerprint genes.

In another aspect of the present invention, a method of diagnosing disease in a patient comprises: performing a multilayer PCA classification on patients' biological samples to extract a set of fingerprint feature genes for specific disease and cell type, tabulating the fingerprint gene information in a database that will be referenced to execute the embodiments of the invention.

The present invention will be able to confirm existence of disease if any, and identify the stage of the disease; provide near real time (4-5 hours) diagnosis of disease at early stages (prescreening); provide identification feature genes that are specific to the disease, the stage of the disease, and the type of cell/tissue all of which will enable prompt therapies in response to the diagnosis.

Other aspects of the invention include extraction of features and performing classification in many other types of high dimensional data.

The present invention will show improvement over currently used classification techniques in terms of efficient dimensionality reduction that reduces computational burden, and feature selection through identification of fingerprint genes that can be used to accurately diagnose and treat diseases.

These and other features, aspects and advantages of the present invention will become better understood with reference to the following drawings, descriptions and claims.

BRIEF DESCRIPTION OF THE DRAWINGS

FIG. 8 shows scatter plots from PCA-Layer 4 indicating the working of the invention and the capability of execution of the several Embodiments 1, 2, 3 and 4 of the invention. FIG. 8c shows that the incoming test patient (marked by the arrow) has the same health status as the true positive data selected from the fingerprint gene database. FIG. 8d shows that the incoming test patient (marked by the arrow) has different health status from the true positive data selected from the fingerprint gene database. True positive data can be a specific disease being tested for in the incoming patient.

DETAILED DESCRIPTION OF THE INVENTION

Figure 1:
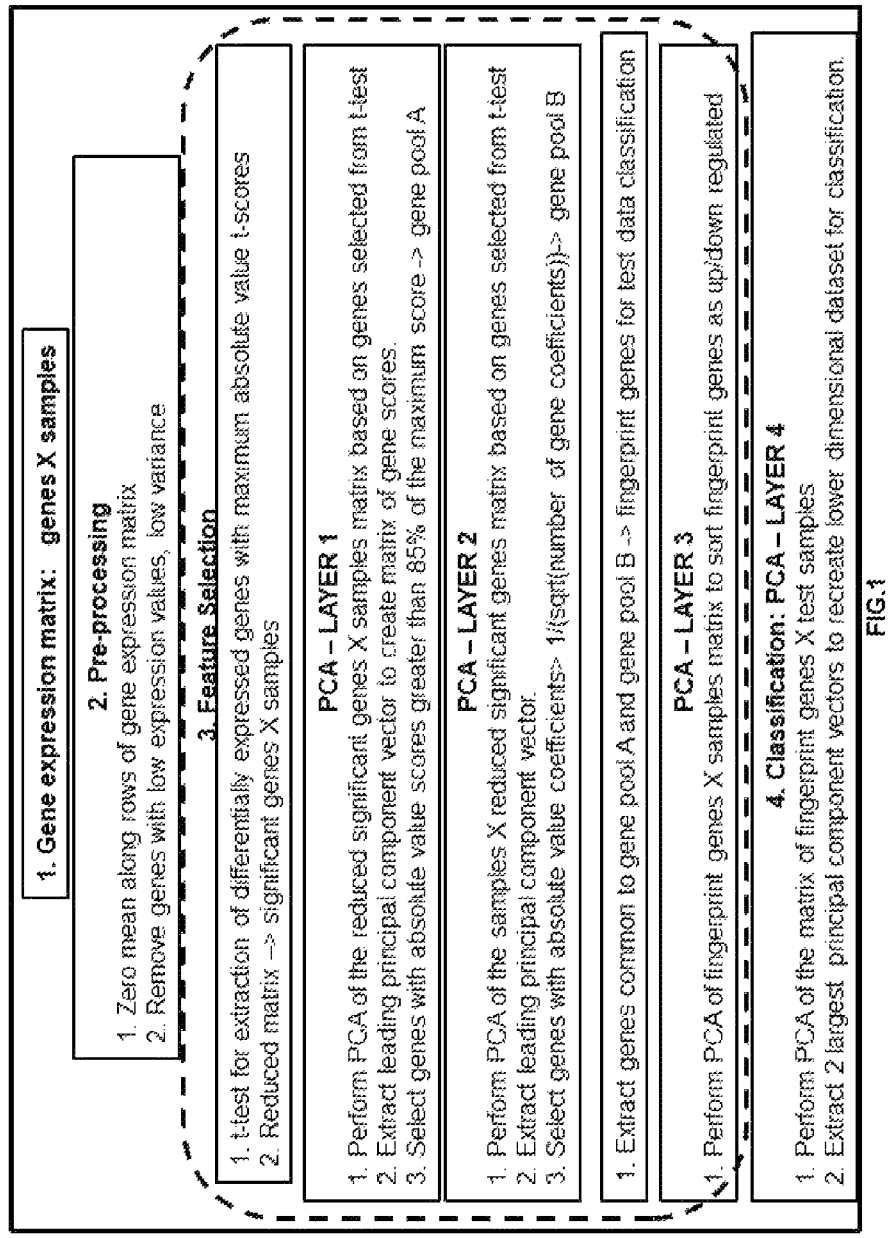
FIG. 1 is a flow chart of the present invention including Step #1-Step #4 of the invention namely, data acquisition, preprocessing, feature (fingerprint genes) selection and classification.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention applies Principal Component Analysis (PCA) as a feature selection and dimensionality reduction tool as well as a classification technique, through a multi-layer supervised learning approach. PCA is a statistical technique that can help identify patterns in high dimensional data, and has several applications in various fields. PCA is manly noted for reducing the data dimensionality by projecting the data in fewer dimensions. The present invention applies PCA for feature extraction rather than feature reduction, which is how PCA has conventionally been applied. While feature reduction simply reduces the dimensionality at the risk of losing some information, feature extraction focuses on extracting those vital features that contribute to the largest variability in the data.

Microarray—a high throughput genomic technology is a powerful tool that has rapidly increased as an investigational method in medical research, since they measure the expression of thousands of genes simultaneously on a genome-wide scale. Gene expression analysis reveals distinct patterns in the expression profile that can help differentiate the disease state from healthy controls. Determining gene expression regulation may be particularly important for understanding the pathological basis of a disease in which multiple systems are affected. The present invention applies a multilayer PCA technique on microarray data comprising of gene expression profiles of subjects, to extract a small subset of the key features/genes that can discriminate between disease and healthy subjects. This technique not only extracts key genes that can be used as fingerprint genes specific to the diagnosis of a disease, but also addresses the dimensionality problem associated with the big data, and even provides a visual classification of the subjects into classes—disease or healthy. Each layer of the PCA is tuned to identify the fingerprint genes that are specific to each disease. The present invention uses each PCA layer to decompose the matrix at each stage and extract the features by using specific selection criteria and adaptive thresholds as necessary.

The present invention is different from what currently exists. Currently, there are several classification algorithms such as Linear Regression, Linear Discriminant Analysis, Nearest Centroid, K-Nearest Neighbors, K-Means Clustering and Hierarchical Clustering (clustering based classifiers), Artificial Neural Networks (ANN), Support Vector Machines (SVM), and other Machine Learning Algorithms. The choice of a classification algorithm is based on the number of training examples, the dimensionality of the feature space, the linear separability of the data, the independence of the features, and the speed/performance/memory usage. SVM have the advantage of good performance of non-linearly separable data and high dimensional data, but could be challenging to train. Also, working with high dimensional data can be computationally intensive. The multilayer PCA method in the present invention attempts to circumvent the dimensionality problem by performing a linear transformation of the data into principal components that express the variability in the data, without loss of information, from which key feature are then extracted/selected yielding the fingerprint features that can then be used to perform the classification. This reduces the computational burden, while at the same time performs feature selection, and is able to achieve over 90% accuracy in its classification. The multilayer PCA classifier can be used for diagnosing and early disease screening based on gene expression profiles by creating a Fingerprint Gene Database as outlined in the several embodiments. While this present method explained in the invention is pertaining to the selection of genes as the features, the technique in this invention can be extended to the selection of other features in other types of data as the case may warrant.

There are several problems associated with other such techniques in the field of the present invention. A classification algorithm's performance is based on the number of training examples, the dimensionality of the feature space, the selection of key and significant features, the linear separability of the data, the independence of the features (genes), and the speed/performance/memory usage. Using optimal genes/features to predict the class of a subject—disease or no disease, will increase the sensitivity, specificity and overall accuracy of the classification algorithm. Computationally intensive techniques such as 'gene shaving' are used for identifying distinct sets or clusters of genes with similar expression patters, while conventional PCA technique has been used as dimensionality reduction technique (rather than feature selection) and for visualization or clustering.

Current techniques do not perform well due to several reasons. While current techniques do perform classification, the initial challenge lies in training the classifier as in the case of SVM, which requires selecting the features/genes. The performance of a classifier is largely dependent on the features (in this case the genes) used for the purpose of training it first. However, some current systems perform feature selection by clustering genes with similar profiles to understand the biological pathways in the disease, while others use computationally intensive techniques to reduce the features. SVM classifies based on the features that are provided to it. Although these methods serve the purpose of classification, there is still the need for a simple, less computationally intensive and accurate technique for the sole purpose of feature selection to train a classifier. Most classifiers will perform well as long as optimal features are used in the training. The challenge is to identify the specific features that enable the classifier to improve performance and accuracy. Also, identification of the features (genes) that are altered in their expression profile during the disease stage, helps understand the disease in the genetic level, and allows for personalized medicine and treatment.

The present invention is an improvement on what currently exists. The present invention uses a multilayer PCA technique, wherein the initial PCA layers are used to select the features or fingerprint genes, and the final PCA layer performs the classification of the subjects into disease vs. non-disease. While this technique not only extracts the key fingerprint genes associated with the disease, it is also able to reduce the computational load during the classification process by using the minimum genes required for classification while maintaining high accuracy. This feature selection technique can be extended to the selection of other features as the data matrix and application changes.

Figure 2:
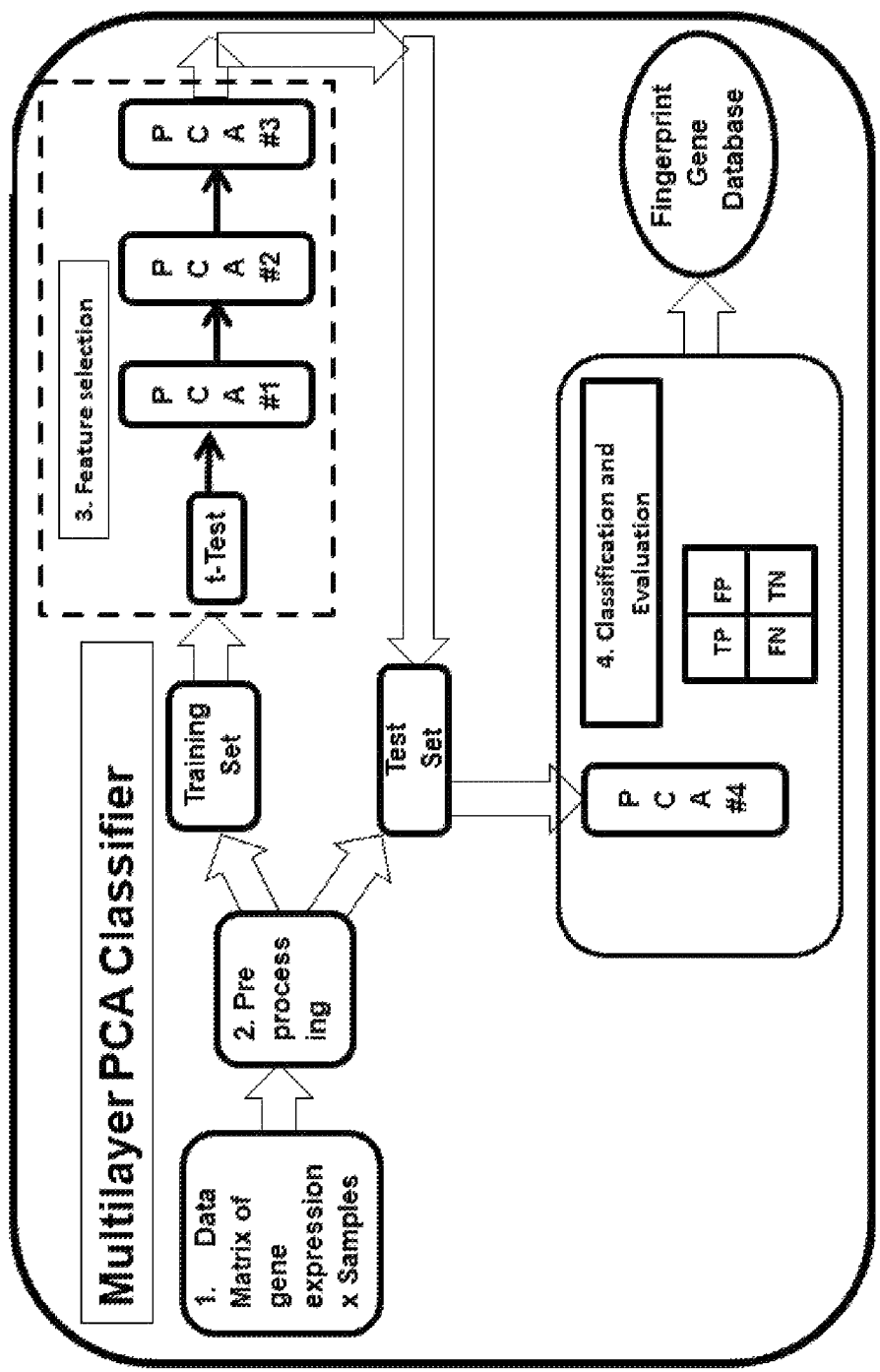
FIG. 2 is a block diagram of the Multilayer PCA Classifier and the overall relationship between the components of the invention including data acquisition, preprocessing, feature selection and classification/evaluation stages to create the fingerprint gene database.
Figure 3:
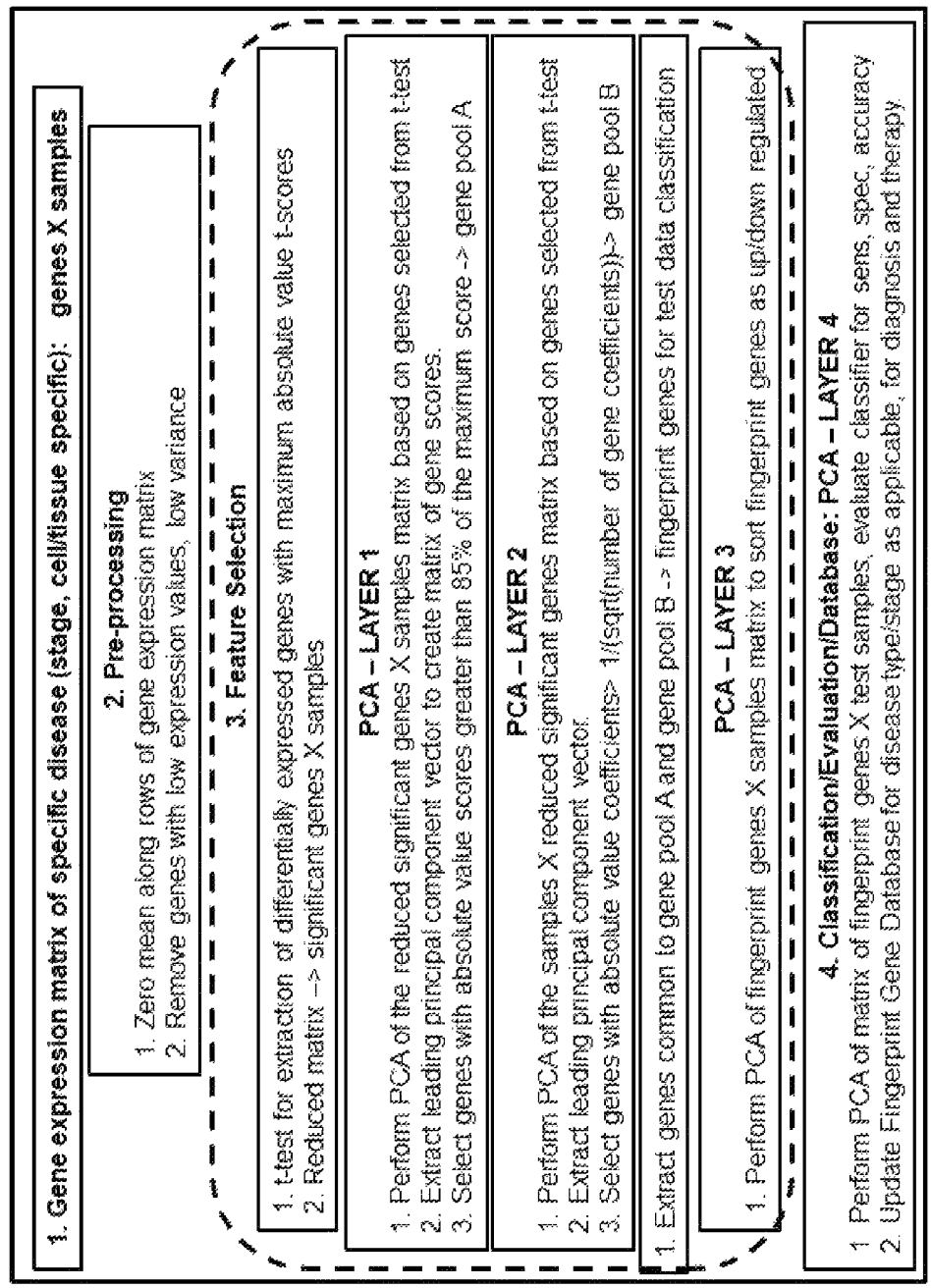
FIG. 3 is a flow chart of an embodiment of the present invention showing the creation of the Fingerprint Gene Database using the multilayer PCA classifier.
Figure 4:
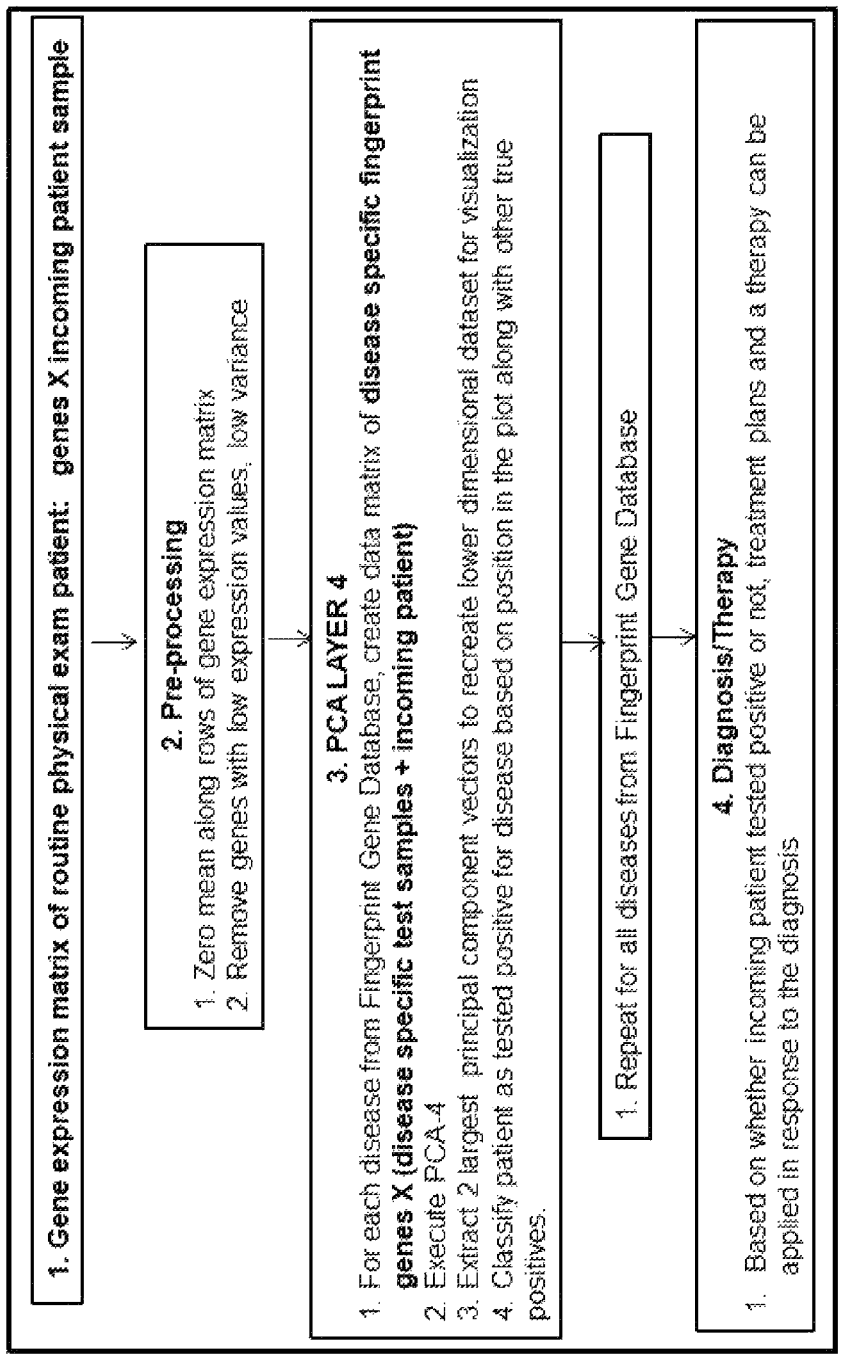
FIG. 4 is a flow chart of an embodiment of the present invention outlining the diagnostic procedure for disease diagnosis during routine physical screening of a patient.
Figure 5:
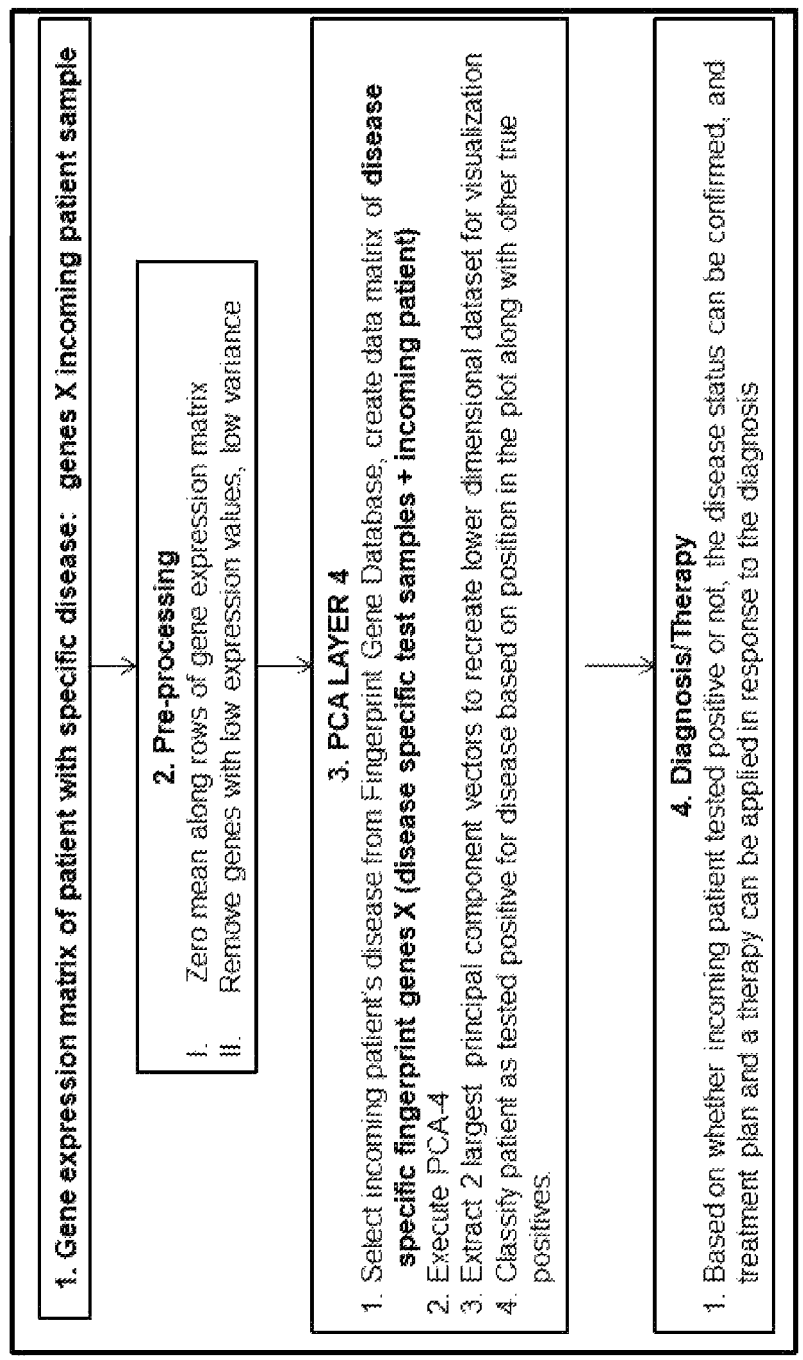
FIG. 5 is a flow chart of an embodiment of the present invention outlining the diagnostic procedure for confirmation of disease in a patient
Figure 6:
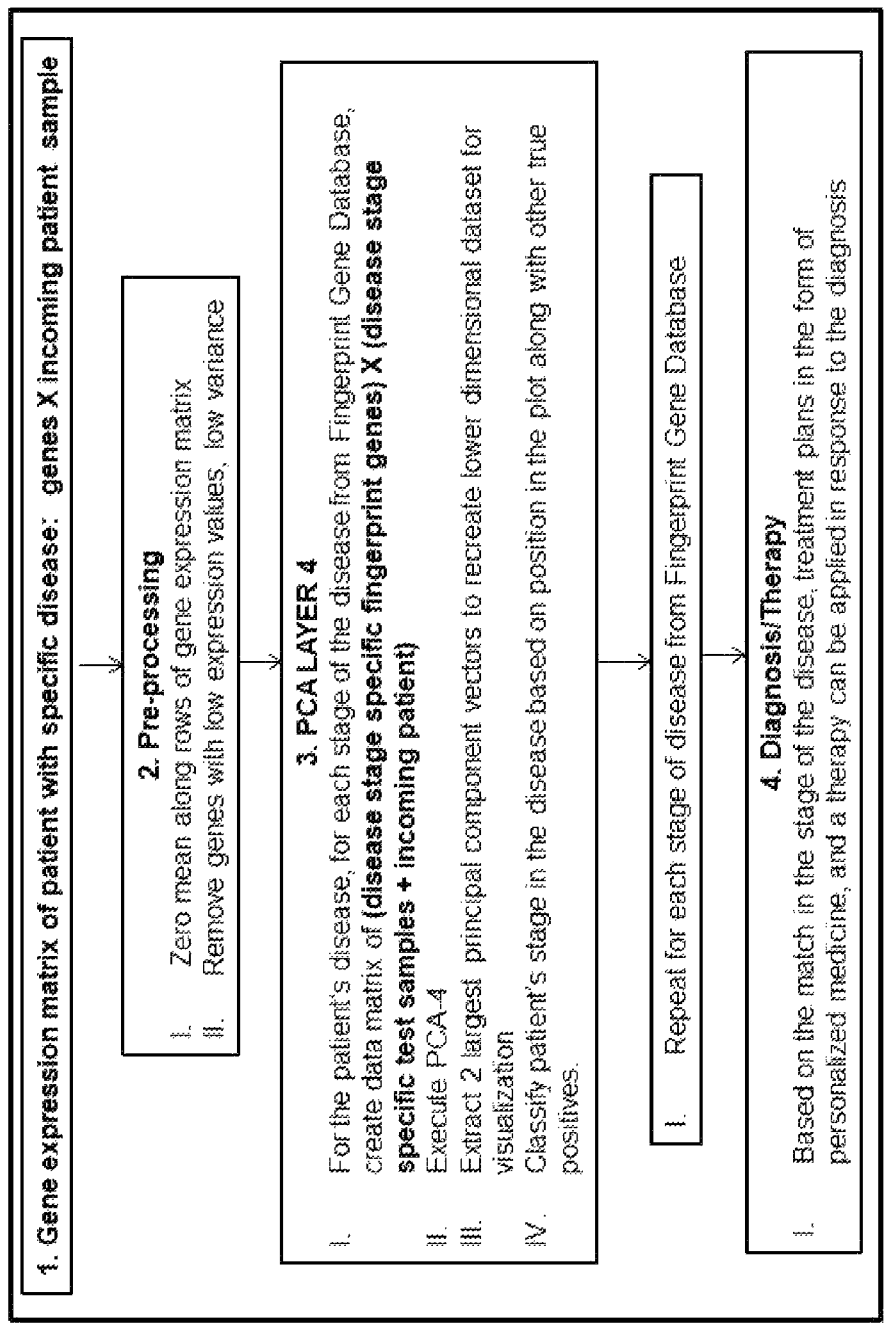
FIG. 6 is a flow chart of an embodiment of the present invention outlining the diagnostic procedure used to identify the stage of disease in a patient.

Referring to FIG. 1, a flow chart of an embodiment of the present invention including Step #1-Step #4 of the invention namely, data acquisition, preprocessing, fingerprint gene (feature) selection and classification is described below. FIG. 2 is a block diagram of the multilayer PCA Classifier showing the overall relationship between the components of the invention and the creation of the Fingerprint Gene Database.

1. DATA ACQUISITION: The invention which was implemented and tested using MATLAB (computer language for signal processing) consists of two parts. The first part involves training the classifier using gene expression profiles with known characteristics. The second part involves testing and validation using the information from the training stage. The biological data for training and testing can be acquired from Gene Expression Omnibus (GEO), a public repository provided by the National Center for Biotechnology Information (NCBI) or any such similar research facility, and this does not change the working of the present invention. This DNA microarray data is in the form of a matrix of about 20,000 genes by human subject biological samples, comprising of gene expression profiles of samples with known disease/control characteristics, which is then subject to preprocessing. Controls refer to control samples that belong to healthy subjects that are known to have no evidence of the specific disease in the disease sample.

2. PRE-PROCESSING: This stage is essentially used to standardize the data and reduce skewness in the data. The order of the steps in the preprocessing stage does not change the working of the invention. Preprocessing involves performing a log based transformation to reduce skewness and produce a more uniformly distributed data, followed by subtracting the mean and dividing by the standard deviation to overcome the aberrations due to variations in experimental conditions from microarray to microarray, normalizing the gene expression values across the samples, and filtering out those genes with very low expression values across the samples and with small variance across the samples.

3. FEATURE SELECTION—t-Test, PCA-Layer 1, PCA-Layer 2, PCA-Layer 3 t-Test: This pre-processed data was then subject to a statistical test such as the t-test, to eliminate statistically insignificant genes. The t-test selects those genes that are differentially expressed with a p-value <0.00001. This is achieved by selecting about 100 genes with most negative t-scores, and about 100 genes with most positive t-scores. From the initial set of genes, the data was now reduced to about 200 (N) statistically significant genes after the t-test. This estimate of about 200 genes is not a hard limit, as the number of genes is adaptive, based on the result of the t-Test's normal quantile plot and histogram plot. The t-scores, p-values and number of significant genes will enable an appropriate threshold to be set to select the differentially expressed N genes.

PCA—Layer 1: The reduced matrix R of (using N statistically significant genes from the t-test) N genes X P samples is then passed into the first PCA layer henceforth referred to as PCA-Layer 1. PCA-Layer 1 performs a linear transformation of the data and creates principal component orthogonal vectors, where each principal component accounts for some variability in the data.

Arrange the matrix R as N genes X P samples matrix, and perform a linear transformation of the data to create principal component vectors (either by eigenvalue decomposition using the P X P covariance matrix or by singular value decomposition). The 'principal sample components' indicates the categories of the samples that best explains the behavioral patterns of the genes. Extract leading principal component vector V to create a matrix of gene scores S=RV.

$$S = RV \quad (1)$$

Compute the cutoff score as 85% of the maximum gene score. Genes with absolute value scores greater than the cutoff score is categorized as gene pool A. Thus genes with absolute value scores greater than about 85% of the maximum score is categorized as gene pool A. This cutoff score of 85% of the maximum gene score may be modified if necessary. Generally, the cutoff score is adaptive and maintained between 60% to 85%.

PCA—Layer 2: The transpose of the reduced matrix R (using N statistically significant genes from the t-test) of P samples X N genes is then passed into the second PCA layer henceforth referred to as PCA-Layer 2. PCA-Layer 2 performs a linear transformation of the data and creates principal component orthogonal vectors, where each principal component accounts for some variability in the data.

Arrange the transpose of matrix R as P samples X N genes matrix, and perform a linear transformation of the data to create principal component vectors (either by eigenvalue decomposition using the N X N covariance matrix or by singular value decomposition). Each component vector consists of weights or regression coefficients corresponding to each feature (gene). Thus, the total number of gene coefficients is the number of gene coefficients in each component. The 'principal gene components' indicates the characteristics of the genes that results in the respective responses in the samples. Extract leading principal component vector consisting of the coefficients of the linear combinations of the genes. Genes with absolute value coefficients greater than 1/(sqrt(total number of gene coefficients in the component)) are categorized as gene pool B.

$$\text{Absolute value of coefficient greater than } 1/(\text{sqrt(total number of gene coefficients in the component))} \quad (2)$$

Genes common to gene pool A (PCA-Layer 1) and gene pool B (PCA-Layer 2) are now referred to as fingerprint genes C. A fingerprint gene is a gene that is differentially expressed in the disease sample compared to the control sample by being either significantly upregulated (overexpressed) or downregulated (underexpressed), as defined by the thresholds set by the multilayer PCA classifier in PCA-Layer 1 and PCA-Layer 2 for acquiring the list of genes in Gene Pool A and Gene Pool A. In order to classify the fingerprint genes as upregulated or downregulated, the matrix of C fingerprint genes X P samples is subject to the third PCA layer PCA-Layer 3.

PCA—Layer 3: The matrix of C fingerprint genes X P samples undergoes a linear transformation to create principal component vectors (either by eigenvalue decomposition using the P X P covariance matrix or by singular value decomposition). Extract leading principal component vector for the gene scores of the fingerprint genes. Genes with positive valued scores are those that are either highly over expressed (upregulated), while negative valued scores are those that are under expressed (down regulated) in disease conditions as compared to normal healthy state. It is to be noted that the t-test in the feature selection stage is a statistical test to identify differentially expressed genes, and any statistical test similar to the t-test that achieves this purpose can be used, and this does not change the working of the present invention. The number of genes selected in this test is dependent on the p-value, and changing the p-value or the resulting number of down selected genes does not change the working of the invention. Also, the fingerprint genes selected as a result of the PCA-Layer 1 and PCA-Layer 2 is a function of equation (1) and (2), and may vary, and this does not change the working of the invention. PCA-Layer 3 involves sorting the fingerprint genes as upregulated or downregulated.

4. Classification

PCA—Layer 4: After subjecting test data to the preprocessing stage, the data matrix of K test samples X C fingerprint genes, is subject to the PCA-Layer 4 which creates principal component orthogonal vectors (either by eigenvalue decomposition using the C X C covariance matrix or by singular value decomposition). Out of these principal components, the top 2 components corresponding to the largest variance are selected and combined with the input data matrix of the fingerprint genes and samples, to recreate a lower dimensional dataset for visualizing, classifying, or testing and validation of the data. The scatter plot of the graph would indicate the classification of the sample subjects as disease or healthy, on either side of the trend line. Based on the use of the invention, the Step #4 could be for testing/validation/ evaluation, or for creating the fingerprint gene database, or for classification as the embodiments depict. This stage of the invention consisting of PCA-Layer 4, is dependent on the number of genes selected by PCA-Layer 1 and PCA-Layer 2 output, and any such dependent changes does not change the working of the invention. Although the present invention focuses on the selection of genes as features, the technique may be extended to the selection of other features based on the available data and requirements in a different application or scenario.

The goal of the present invention attempts to help the general population have access to health pre-screening for major diseases and conditions that makes them better positioned for early treatment options leading to improved prognosis. To achieve this goal, this invention can be executed through various embodiments, each of which serves a specific purpose. The several embodiments are explained in the following steps. Referring to FIG. 3 through FIG. 6, the present invention includes several embodiments that can be executed for diagnosing disease as mentioned. The multilayer PCA classifier used in the embodiments requires software processing using MATLAB as the computer language, on any high speed computer with internet access. Any software processing language can also be used in place of MATLAB to execute the algorithm used by the classifier.

Embodiment 1—Creation of Fingerprint Gene Database (FIG. 3): In this embodiment the goal is to extract fingerprint genes specific to the disease, that can be tabulated as a library or lookup-table of disease-specific genes that can be used for future disease classification and for analysis of gene ontology (molecular function, biological pathways, cellular component). This information can be stored and accessed through a website. Embodiment 1 is executed and updated for as many diseases as permitted by available DNA microarray data (in NCBI), and the results comprising of disease specific fingerprint genes is archived for future use by physicians (embodiments 2, 3, 4) and researchers. Especially in the case of diseases such as cancers, the library or lookup-table can also tabulate the level of differential expression and fold change of those fingerprint genes for the different stages of the cancer. Also, this embodiment can be used to tabulate tissue/cell specific gene expression levels for each disease, disease stage and disease type. This information will be extremely beneficial where patients have to be provided personalized medicine. A fingerprint gene is a gene that is differentially expressed in the disease sample compared to the control sample by being either significantly upregulated (over expressed) or downregulated (under expressed), as defined by the thresholds set by the multilayer PCA classifier in PCA-Layer 1 and PCA-Layer 2 for acquiring the list of genes in Gene Pool A and Gene Pool A. Fingerprint genes are both statistically as well as biologically significant. Using PCA-Layer 3, this embodiment also tabulates the regulation of the fingerprint genes as to whether the specific fingerprint gene is up or down regulated. The Steps #1-#3 of this embodiment could be referred to as the training stage, while Step #4 could be referenced as the test/validation or classification stage.

Step #1. Data Acquisition: Acquire microarray data from any public repository such as GEO from NCBI, of subjects with known characteristics, comprising of approximately equal number of control samples and disease samples with a specific disease/condition, specific stage of the disease/ condition, and the treatment phase of the disease/condition. This data will be acquired in a matrix format comprising of genes by samples. In the matrix of expression data (gene expression data matrix), A, each row corresponds to a different gene and each column corresponds to one of several different conditions/samples to which the cells were exposed. The alt entry of the matrix contains the $i^{th}$ gene's relative expression ratio with respect to a control population for sample t.

Step #2. Preprocessing: This involves performing a log based transformation on the acquired data to reduce skewness and produce a more uniformly distributed data; subtracting the mean and dividing by the standard deviation to overcome the aberrations due to variations in experimental conditions from microarray to microarray; normalizing the gene expression values across the samples, and filtering out those genes with very low expression values across the samples and with small variance across the samples. Specifically, log base 2 transform was used to observe the fold change. This data is split into a training set of P samples (two-third of the samples to use in Step #1-Step #3) and a test/validation set of K samples (one-third to use in Step #4). This method of splitting the data is also known as the Holdout method. Step #3. Feature Selection (t-test, PCA-Layer 1, PCA-Layer 2, PCA-Layer 3): This training set from the pre-processed data is subject to a statistical test such as the t-test, to eliminate statistically insignificant genes. The t-test gives the t-score and p-value for each gene. The test statistic for comparing two groups is the t-statistic: $t=(x_{i,1}-x_{i,2})/s_i$, where $x_{i,1}$ is the mean value of gene i in the data group 1, $x_{i,2}$ is the mean in data group 2, and $s_i$ is the standard error for gene i. The greater the magnitude of 't' (can be positive or negative) the greater the evidence that those genes are differentially expressed. The top genes with largest magnitude t-scores and with a p-value<0.00001 are selected. From the initial set of genes, the data is now reduced to the top statistically significant genes N after the t-test. This estimate of top statistically significant genes is not a hard limit, as the number of genes is adaptive, based on the result of the t-Test's normal quantile plot and histogram plot. The t-scores, p-values and number of significant genes will enable an appropriate threshold to be set to select the differentially expressed N genes The reduced matrix R (using N statistically significant genes from the t-test) of significant N genes X P samples is then passed into the first PCA layer PCA-Layer 1. PCA-Layer 1 performs a linear transformation of the data and creates principal component orthogonal vectors, where each principal component accounts for some variability in the data. Arrange the matrix R as N genes X P samples matrix, and perform a linear transformation of the data to create principal component vectors (either by eigenvalue decomposition using the P X P covariance matrix or by singular value decomposition). The 'principal sample components' indicates the categories of the samples that best explains the behavioral patterns of the genes. Extract leading principal component vector V to create a matrix of gene scores S=RV. Genes with absolute value scores greater than 85% of the maximum score (subject to adaptation if necessary) is categorized as gene pool A.

Arrange the matrix R as P samples X N genes matrix, to pass into the second PCA layer PCA-Layer 2. PCA-Layer 2 performs a linear transformation of the data to create principal component vectors (either by eigenvalue decomposition using the N X N covariance matrix or by singular value decomposition). Each component vector consists of weights or regression coefficients corresponding to each feature (gene). The 'principal gene components' indicates the characteristics of the genes that results in the respective responses in the samples. Extract leading principal component vector consisting of the coefficients of the linear combinations of the genes. Genes with absolute value coefficients greater than 1/(sqrt(total number of gene coefficients in the component)) are categorized as gene pool B.

Genes common to gene pool A and gene pool B are now referred to as fingerprint genes C. Create a new matrix of C fingerprint genes X P samples that is further reduced in size, and used as input to the third PCA layer PCA-Layer 3. Arrange the matrix as C feature genes X P samples, and perform a linear transformation of the data to create principal component vectors (either by eigenvalue decomposition using the P X P covariance matrix or by singular value decomposition). Extract leading principal component vector to create a matrix of gene scores for the feature genes. Genes with positive valued scores are upregulated, while genes with negative valued scores are down regulated.

These fingerprint genes could be used as potential identifiers to classify the particular disease, and also provide vital gene expression information related to upregulation and down regulation, for the particular stage of the disease. Hence a test/validation is necessary to authenticate the selected features before storing the information in a library.

Step #4. Classification/Evaluation/Database: This stage uses the test/validation data which was set aside in Step #2 after preprocessing. This stage involves using the selected C fingerprint genes from the PCA-Layer 1, PCA-Layer 2 layers to validate the test data. The test data matrix is now made up of a matrix of the K test samples set aside after the preprocessing and the selected C fingerprint genes in Step #2 (test samples X fingerprint genes). This reduced matrix composed of K test samples by C fingerprint genes, is subject to the PCA-Layer 4 layer, which creates principal component orthogonal vectors (by the mathematical process of eigenvalue decomposition using C by C covariance matrix or singular value decomposition). Out of these principal components or eigenvectors, the top 2 components/eigenvectors corresponding to the largest 2 variances are selected and combined with the input data matrix of the fingerprint genes and test samples (by matrix multiplication), to recreate a lower dimensional dataset for visualizing the data. The scatter plot would indicate the classification of the sample subjects as disease or healthy, on either side of the trend line. Each dot on the scatter plot is a patient sample, whose location on either side of the trend line indicates whether the subject was classified as disease or healthy. If the patient subject sample is classified as disease on the disease side of the trend line, then the sample is classified correctly. Similarly, if the control subject sample is classified as a control on the control side of the trend line, then the sample is classified correctly. These would then be classified as true positives. From the plot True Positives (TP), True Negatives (TN), False Positives (FP) and False Negatives (FN) are selected and the sensitivity, specificity and accuracy of the classifier are computed for the data set as shown in Table 1. The classifier performance was evaluated to assess its capability to discriminate between disease and control samples. Overall, the Multilayer PCA classifier performed at a sensitivity of 92%, specificity of 90%, and accuracy of 90%. Based on the accuracy, sensitivity and specificity values of at least 90%, the fingerprint genes are stored in a library of gene data to use as a discriminative set of genes in any classifier, for classifying/identifying/predicting that specific disease. A fingerprint gene is a gene that is differentially expressed in the disease sample compared to the control sample by being either significantly upregulated (overexpressed) or downregulated (underexpressed), as defined by the thresholds set by the multilayer PCA classifier. For each disease type (and stage of disease as applicable) the list of fingerprint genes is stored in a library/lookup table as sorted up/down regulated genes for that specific disease (Fingerprint Gene Library), along with the matrix of fingerprint genes X test samples (Fingerprint Gene Data Matrix). Essentially, the Fingerprint Gene Data Matrix would be a matrix of gene expression data with rows of fingerprint genes' expression levels vs. the columns of the human patients' biological samples for the specific disease and cell/type This Fingerprint Gene Library and Fingerprint Gene Data Matrix together make up the Fingerprint Gene Database. The Fingerprint Gene Library and Fingerprint Gene Data Matrix constituting the Fingerprint Gene Database can be made accessible through a website, and updated as more diseases are analyzed/tested/validated using Embodiment 1. Embodiment 1 can be used to create this reference database to acquire information for executing Embodiments 2, 3, 4 which will enable early diagnosis and screening, in response to which, appropriate therapy can be administered.

TABLE 1

Sensitivity, Specificity and Accuracy calculations
using true/false positives and true/false negatives
from the plot of PCA-Layer 4 layer.

|  | Disease | Controls |
|---|---|---|
| Test Positive | True Positive (TP) | False Positive (FP) |
| Test Negative | False Negative (FN) | True Negative (TN) |

Sensitivity = TP/(TP + FN)
Specificity = TN/(TN + FP)
Accuracy = (TP + TN)/(TP + FP + TN + FN)

Figure 8A:
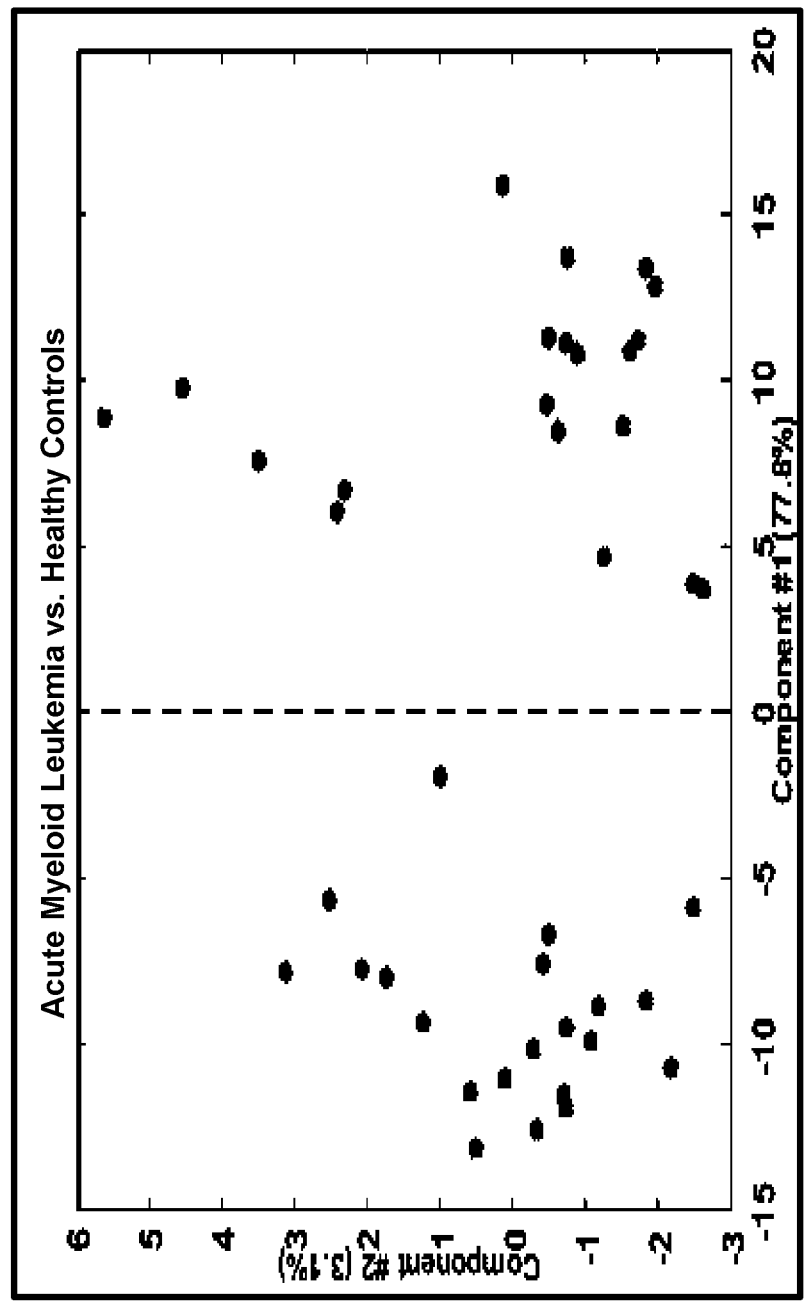
FIG. 8a, 8b are scatter plots showing the working of Embodiment 1 and the efficiency of the Multilayer PCA Classifier in differentiating the subjects into disease and healthy cases on either side of the vertical trend line.
Figure 8B:
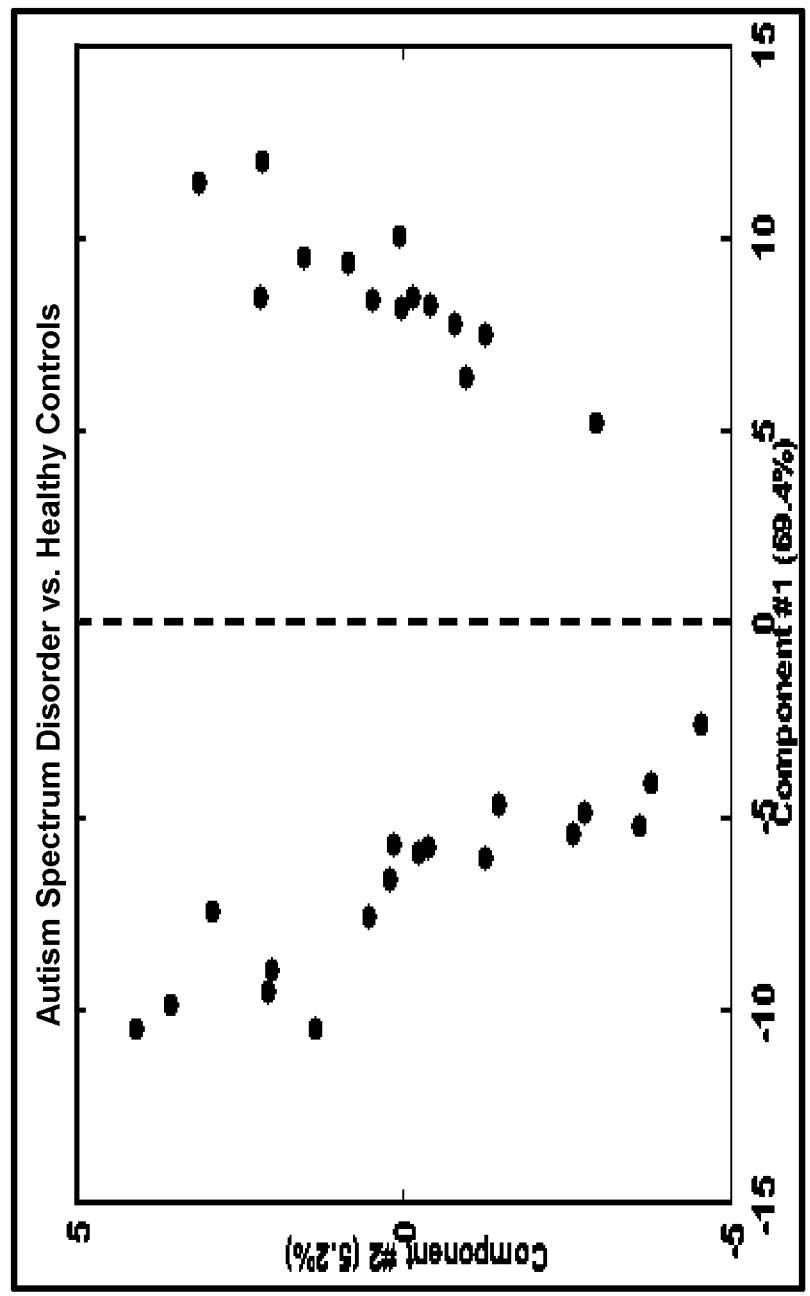
Figure 8C:
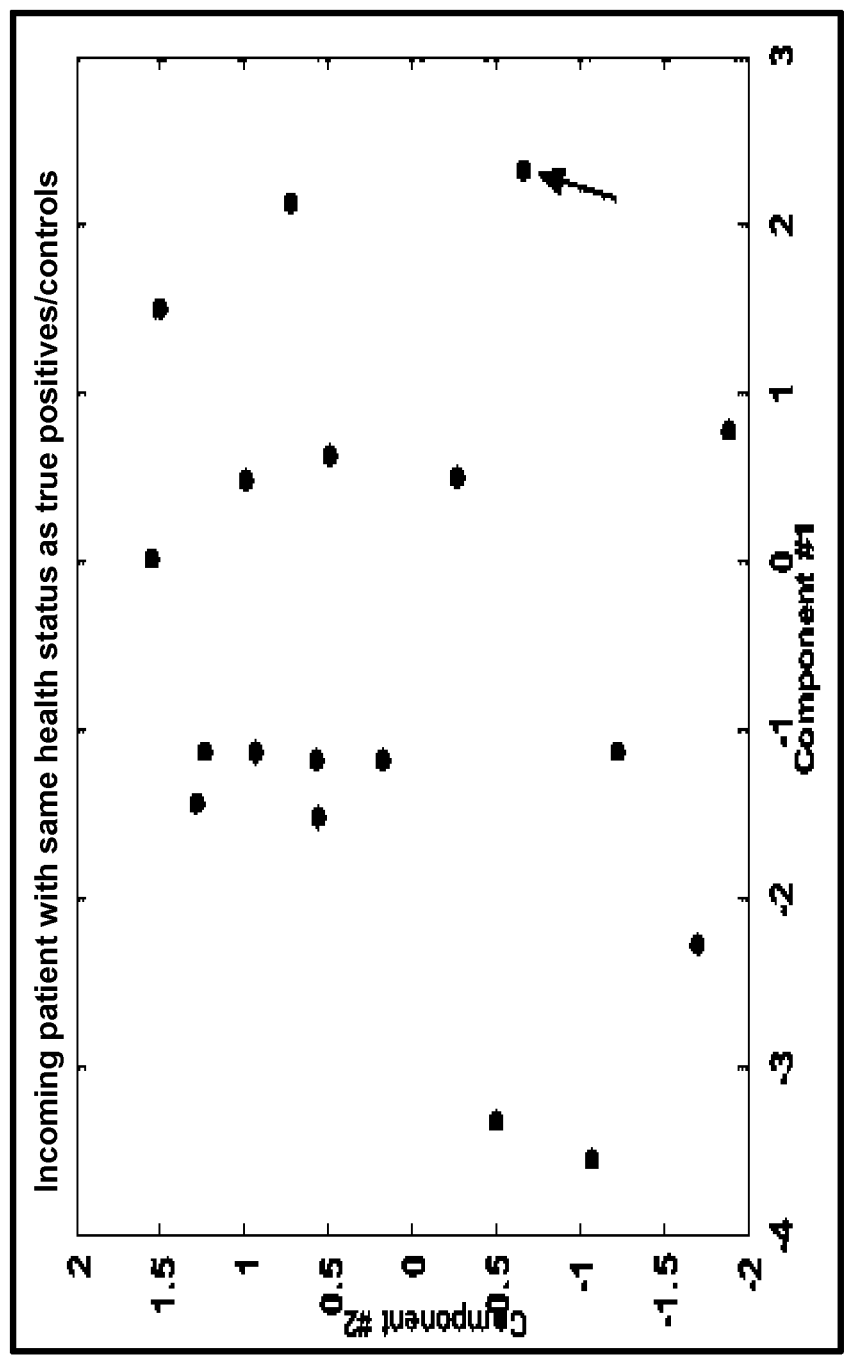
FIG. 8c, 8d are scatter plots showing the working of Embodiments 2, 3 and 4. As shown in the flowcharts of the embodiments 2, 3, and 4 of the invention, PCA-Layer 4 includes a classification of the test patient as disease or healthy based on the visual location of the patient sample on the scatter plot.
Figure 8D:
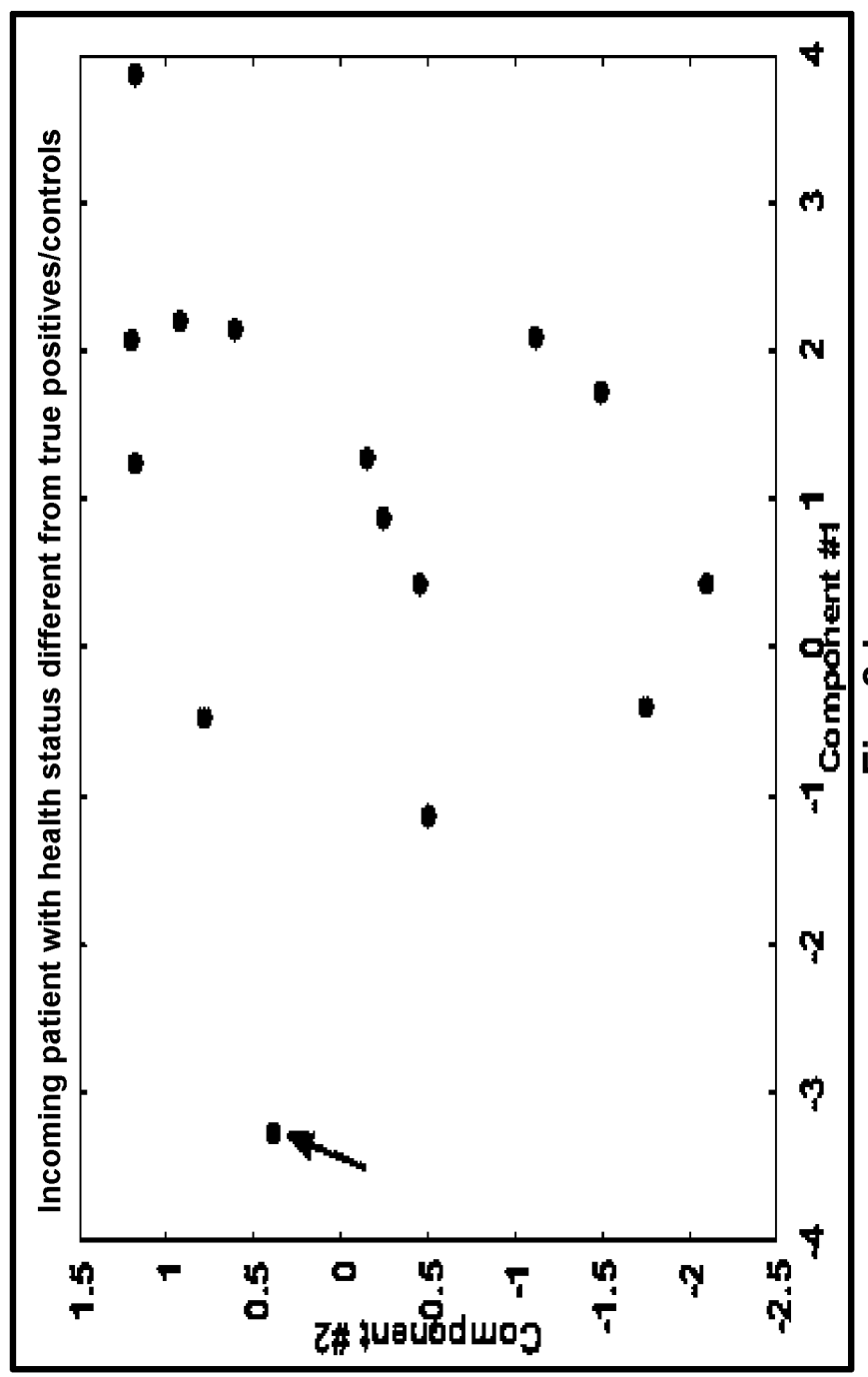

Embodiment 2—Early pre-screening information during patient routine physical exam (FIG. 4): In this embodiment of the invention, the goal is to provide physicians with early pre-screening information during patient routine physical exam. Such a test patient will have to undergo a simple invasive procedure that requires extracting some peripheral blood (venous blood as is usually taken during regular blood work for tests), which is then sent to a laboratory that is capable of processing using microarray technology. The patient's biological sample to extract the gene expression data can be acquired from different cell/tissue type including but not limited to peripheral blood, tissues and cells. The laboratory will then perform the microarray experiment using the test patient's blood sample, perform a log based transformation on the acquired data to reduce skewness and produce a more uniformly distributed data, subtract the mean and divide by the standard deviation to overcome the aberrations due to variations in experimental conditions from microarray to microarray thus normalizing the gene expression values across the samples, and provide a data matrix of gene expression profile data for that test patient. For each disease available in the Fingerprint Gene Database (cancers, Alzheimers, autism etc) the fourth PCA layer PCA-Layer 4 is executed using the fingerprint genes for that specific disease created in Fingerprint Gene Database in Embodiment 1. The data matrix will be composed of samples by disease specific fingerprint genes. The samples will include true positives or controls and the test patient. If the test patient has the specific disease, the result of the PCA-Layer 4 plot will classify the test patient as diseased along with the other such true positives/controls. If the test patient does not have the disease, the result of the PCA-Layer 4 plot will classify the test patient as a separate sample on the plot, indicating that the test patient does not have that specific disease. FIG. 8c is a scatter plot of such a situation where the incoming patient had a health condition that matched the true positives or controls, showing his/her location ((position of the dot indicated by the arrow) amidst the other true positives or controls. FIG. 8d is a scatter plot of such a situation where the incoming patient had a health condition that does not match the true positives or controls, showing his/her location (position of the dot indicated by the arrow) away from the other true positives or controls. Thus, the location of the patient's position on the plot will add to the visualization and diagnosis of the disease if any. By executing the multilayer PCA classifier through the consolidated lists of disease specific fingerprint genes, the test patient's health condition can be identified in a few hours (about 4-5 hours), and based on the results, a therapy or medical treatment and follow up plans can be started immediately as required.

Embodiment 3—Confirmation of disease or second opinion (FIG. 5): In this embodiment of the invention, the goal is to provide physicians information regarding any patient who has been diagnosed with a particular disease such as cancer, but requires a confirmation or second opinion at the genetic level. Such a patient will have to undergo a simple invasive procedure that requires extracting some peripheral blood (venous blood as is usually taken during regular blood work for tests), which is then sent to a laboratory that is capable of processing using microarray technology. The patient's biological sample to extract the gene expression data can be acquired from different cell/tissue type including but not limited to peripheral blood, tissues and cells. The laboratory will then perform the microarray experiment on the test patient's blood sample, perform a log based transformation on the acquired data to reduce skewness and produce a more uniformly distributed data, subtract the mean and divide by the standard deviation to overcome the aberrations due to variations in experimental conditions from microarray to microarray thus normalizing the gene expression values across the samples, and provide a data matrix of gene expression profile data for that test patient. The fourth PCA layer, PCA-Layer 4 is then executed using the fingerprint genes for that specific disease of the test patient, from the Fingerprint Gene Database created in Embodiment 1. The data matrix will be composed of samples by disease specific fingerprint genes. The samples will include true positives/ controls and the test patient. If the test patient has the specific disease, the result of the PCA-Layer 4 scatter plot will classify the test patient as diseased along with the other such true positives/controls. If the test patient does not have the disease, the result of the PCA-Layer 4 plot will classify the test patient as a separate sample on the scatter plot, indicating that the test patient does not have that specific disease. FIG. 8c is a scatter plot of such a situation where the incoming patient had a disease condition that matched the true positives or controls, showing his/her location (position of the dot indicated by the arrow) amidst the other true positives or controls. FIG. 8d is a scatter plot of such a situation where the incoming patient had a disease condition that does not match the true positives or controls, showing his/her location (position of the dot indicated by the arrow) away from the other true positives or controls. Thus the location of the test patient's position on the plot will add to the visualization and confirmation of the diagnosis. By executing the Multilayer PCA classifier through the consolidated list of disease specific fingerprint genes, the test patient's health condition can be confirmed in a few hours (about 4-5 hours), and a therapy or medical treatment and follow up plans can be started immediately as required.

Embodiment 4—Identification of stage of the disease (FIG. 6): In this embodiment of the invention, the goal is to provide physicians with health information regarding any patient who has been diagnosed with a particular disease such as cancer, but more information is required such as the expression levels of the genes related to the stage of the disease, chances of metastasis, response to treatment. Such a patient will have to undergo a simple invasive procedure that requires extracting some peripheral blood (venous blood as is usually taken during regular blood work for tests), which is then sent to a laboratory that is capable of processing using microarray technology. The patient's biological sample to extract the gene expression data can be acquired from different cell/tissue type including but not limited to peripheral blood, tissues and cells. The laboratory will then perform the microarray experiment on the test patient's blood sample, perform a log based transformation on the acquired data to reduce skewness and produce a more uniformly distributed data, subtract the mean and divide by the standard deviation to overcome the aberrations due to variations in experimental conditions from microarray to microarray thus normalizing the gene expression values across the samples, and provide a data matrix of gene expression profile data for that test patient. Based on the up/down regulation levels of disease specific fingerprint genes as stored in the lookup table created using Embodiment 1, the test patients stage in the disease can be identified. The fourth PCA layer, PCA-Layer 4 is executed using the fingerprint genes for that specific stage of that specific disease of the test patient, from the Fingerprint Gene Database created in Embodiment 1. The data matrix will be composed of samples by disease and stage specific fingerprint genes. The samples will include true positives and the test patient. If the test patient is at the specific stage in the disease, the result of the PCA-Layer 4 plot will classify the test patient along with the other such true positives/controls. If the test patient is not at the specific stage in the disease, the result of the PCA-4 plot will classify the test patient as a separate sample on the plot, indicating that the test patient is not at that specific stage in the disease. FIG. 8c is a plot of such a situation where the incoming patient had a disease stage that matched the true positives or controls, showing his/her location (position of the dot indicated by the arrow) amidst the other true positives or controls. FIG. 8d is a plot of such a situation where the incoming patient had a disease stage that does not match the true positives or controls, showing his/her location (position of the dot indicated by the arrow) away from the other true positives or controls The test patient's stage in the specific disease can be identified by the location of the test patient's position on the plot. This information will help expedite treatment options by providing personalized therapy for the test patient, possibly improving the prognosis.

Figure 7:
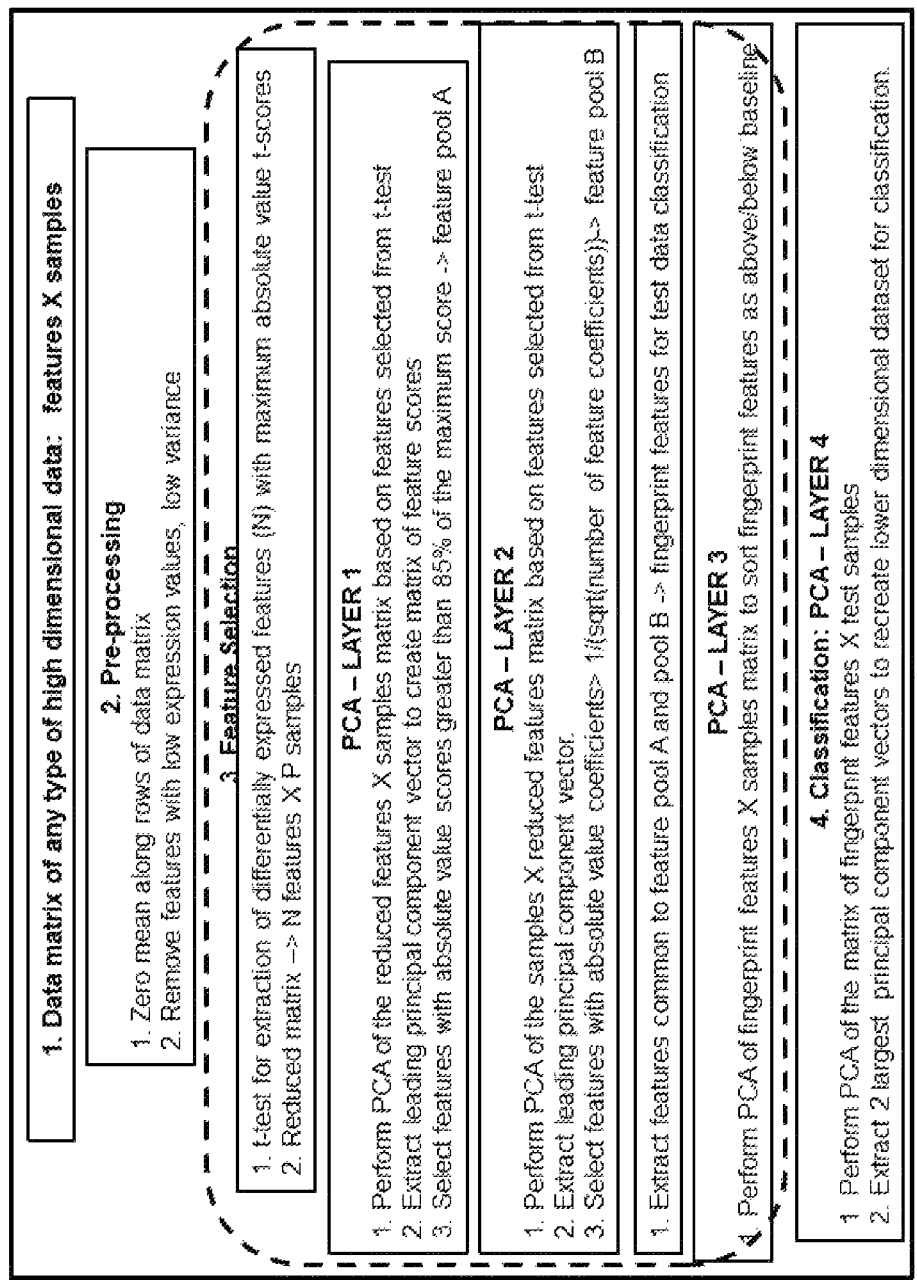
FIG. 7 is a flow chart of an embodiment of the present invention outlining the application of the invention for general purpose high dimensional data feature identification and selection.

Embodiment 5—Any High dimensional Data Sets (FIG. 7): Currently, with improvements in technology large amounts of data are available in different areas of medicine, high resolution imaging and signal processing data, to name a few. In all these situations, the number of features far exceeds the number of observations, creating a dimensionality problem in the multivariate data that can increase computational intensity. The need then arises to reduce the feature space to a subset of precise and specific features that define the condition. Instead of merely performing feature reduction to reduce dimensionality, it is necessary to select the fingerprint features that precisely define the condition. Certain types of cancers are identified based on key morphological patterns in the cells/tissues. These could be key identification marks or features that help distinguish one type/subtype of cancer from another by analyzing the light microscopy imaging data, or any similar imaging data of cells and tissues. Embodiment 5 can be any such high dimensional data that requires classification. The multilayer PCA Classifier can be executed on this data using available truth data, fingerprint features can be selected and used for further classification. Similar to Embodiment 1 which was implemented on genetic data from DNA microarray, Embodiment 5 can be implemented on imaging data to classify the two categories of data into the respective classes. After initial preprocessing of the data matrix, the feature selection consists of the t-test followed by PCA-Layer 1 and PCA-Layer 2 to select the fingerprint features for test data classification. The PCA-Layer 3 can be implemented to sort the fingerprint features as above or below a set baseline depending on the data matrix and application. PCA-Layer 4 will be implemented on the fingerprint features by test samples, to classify the test samples into the two categories defined by the data matrix. As an example, imaging data (pictures) of cancerous tissues and cells can be processed using the multilayer PCA classifier to identify abnormalities in the tissues that will enable the identification of the cancer or disease if present. The PCA-Layer 4 can be used to visualize the samples as normal (healthy/no disease) vs. abnormal (not healthy/cancerous)

As shown in the embodiments of the invention the Step #1-Step #4 outlines the procedure for executing the present invention. The diagnostic procedure requires the use of a high speed computer with MATLAB software, access to internet, and microarray data of the patients and control subjects. As per embodiment 1, the fingerprint gene data needs to be tabulated as a library or lookup table, and requires access to memory storage device. The data for the embodiment can be downloaded from the GEO database into the computer, and the software program for the multilayer PCA classifier will be executed using MATLAB on the data. The diagnosis and results of the analysis can be made available to the physician, laboratory or research facility, and appropriate treatment plans and options can be made available to the patient as needed.

All the steps outlined in the embodiments are necessary for the invention to work. Each embodiment projects a specific use of the invention. Patient specific microarray data or any similar data at the genetic level is required to implement the algorithm used to implement the classifier. This can be accessed from currently available data through the NCBI. In order to store or archive information regarding the fingerprint genes, access to the memory storage device is also necessary. This information needs to accessible to physicians and relevant research facilities or laboratory. A communication system involving the physician, research facility, and algorithm implementers for information exchange will enhance the smooth working of the invention. Regarding any patient who is coming in for a routine physical exam, such a patient will have to undergo a simple invasive procedure that requires extracting some peripheral blood (venous blood as is usually taken during regular blood work for tests), which will then be sent to a laboratory that is capable of processing using microarray technology. Once the blood sample is processed, it will be made available to the algorithm implementers for software processing by executing the Multilayer PCA classifier.

All the embodiments in the present invention can also be implemented using any form of biological data that provides information at the genetic level, and such a change will not affect the working of the invention. Also, the preprocessing stage of Step #2 can be extended beyond, and not be limited to the log transformation, data centering, and normalization. This will not alter the quantitative value of the data, and any additional preprocessing steps will not change the working of the invention. In Step #3 wherein a t-test is used to eliminate statistically insignificant genes, any similar statistical test can also be used instead of the t-test, and this will not alter the working of the invention. The claimed invention executed the Multilayer PCA classifier using MATLAB, and implementing the classifier using a different computer language does not change the objective or working of the invention.

As mentioned, the goal of the present invention attempts to help the general population have access to health pre-screening for major diseases and conditions that makes them better positioned for early treatment options leading to improved prognosis. To achieve this goal, this invention can be executed through various embodiments, each of which serves a specific purpose. Each embodiment in the claimed invention is structured with a goal to provide medical treatment and therapy in response to the diagnosis of the multilayer PCA Classifier.

As outlined in Embodiment 1 of the invention, the goal is to extract fingerprint genes (features), specific to the disease, that can be archived and tabulated as a library or lookup-table of disease-specific genes that can be used for future disease classification and for analysis of gene ontology (molecular function, biological pathways, cellular component). The Fingerprint Gene Database is basically a library or lookup table of the fingerprint gene information along with the corresponding data matrix of the samples. The database for the present invention was created with the available gene expression profile data of different samples for several diseases and cell/tissue types, from Gene Expression Omnibus (GEO) available through the National Center for Biotechnology Information (NCBI). For acquiring further data for executing the embodiments, samples of genetic information from different cell types of patients with specific known diseases will be extracted. This could require taking blood, skin, biopsy tissues, and other such cell types based on the availability of cell types and the specific disease. The genetic information will be extracted using microarray techniques in the laboratory, and made available to implement the multilayer PCA classifier, as explained in Steps #1-#4 of Embodiment 1. This embodiment can then be executed for as many diseases as permitted by available DNA microarray data, and the results comprising of disease specific fingerprint genes can be archived for future use by physicians and researchers. Especially in the case of diseases such cancers, the library or lookup-table can also tabulate the level of differential expression and fold change of those fingerprint genes for the different stages and subtypes of the cancer. Embodiment 1 of the present invention has been executed for several diseases such as but not limited to: Acute Myeloid Leukemia (AML) and its 8 subtypes, cancers of breast, cervical, colorectal, lung, pancreatic, prostate; Autism Spectrum Disorder diagnosed from peripheral blood (leukocytes, lymphocytes, lymphoblastoids), brain (cortex, cerebellum), induced pluripotent stem cells, skin fibroblasts; Neurodegenerative diseases such as Alzheimers, Parkinson, Huntington diagnosed from blood and brain cells. Embodiments 2, 3 and 4 of the invention can use the fingerprint gene information in the Fingerprint Gene Database to execute the multilayer PCA classifier to diagnose patient health status and then provide future treatment and therapy options in response to the diagnosis. This information will be extremely beneficial where patients have to be provided personalized medicine, and an appropriate therapy can be applied in response to the diagnosis.

In Embodiment 2 (Early pre-screening information during patient routine physical exam) of the invention, the goal is to provide physicians and related laboratories with early health screening information regarding any patient who is coming in for a routine physical exam. Such a patient will have to undergo a simple invasive procedure that requires extracting some peripheral blood (venous blood as is usually taken during regular blood work for tests), which is then sent to a laboratory that is capable of processing patient cell samples using microarray technology The laboratory will then perform the microarray experiment on the patient's, and provide a data matrix of gene expression profile data for that patient. This data can be downloaded into the computer that can then execute the multilayer PCA classifier as explained in Steps #1-#4 of embodiment 2. Results of the test will reveal information regarding presence and stage of disease, which can be made available in a few hours (about 4-5 hours), and based on the results, medical treatments and follow up plans can be started immediately. Thus, an appropriate therapy can be applied in response to the diagnosis.

In Embodiment 3 (Confirmation of disease or second opinion) of the invention, the goal is to provide physicians information regarding any patient who has been diagnosed with a particular disease such as cancer, but requires a confirmation at the genetic level. Such a patient will have to undergo a simple invasive procedure that requires extracting some peripheral blood (venous blood as is usually taken during regular blood work for tests), which is then sent to a laboratory that is capable of processing using microarray technology. The laboratory will then perform the microarray experiment on the patient's, and provide a data matrix of gene expression profile data for that patient. This data can be downloaded into the computer that can then execute the multilayer PCA classifier as explained in Steps #1-#3 of embodiment 3. Results of the test confirming or negating the existence of the disease can be made available in a few hours (about 4-5 hours), and based on the results, medical treatments, therapy and follow up plans can be started immediately in response to the diagnosis.

In Embodiment 4 (Identification of stage of the disease) of the invention, the goal is to provide physicians and related laboratories with health information regarding any patient who has been diagnosed with a particular disease such as cancer, but more information is required such as the stage of the disease, chances of metastasis, response to treatment. Similar to embodiment 2, such a patient will have to undergo a simple invasive procedure that requires extracting some peripheral blood (venous blood as is usually taken during regular blood work for tests), which is then sent to a laboratory that is capable of processing using microarray technology. The laboratory will then perform the microarray experiment on the patient's, and provide a data matrix of gene expression profile data for that patient. This data can be downloaded into the computer that can then execute the multilayer PCA classifier as explained in Steps #1-#4 of embodiment 3. The stage of the disease can be identified using the stage specific fingerprint genes. Results of the test can be made available in a few hours (about 4-5 hours), and based on the results, medical treatments, therapies and follow up plans can be started immediately in response to the diagnosis.

Embodiment 5 (Any High dimensional Data Sets): Currently, with improvements in technology large amounts of data are available in different areas of medicine, high resolution imaging and signal processing data, to name a few. In all these situations, the number of features far exceeds the number of observations, creating a dimensionality problem in the multivariate data that can increase computational intensity. The need then arises to reduce the feature space to a subset of precise and specific features that define the condition. Instead of merely performing feature reduction to reduce dimensionality, it is necessary to select the fingerprint features that precisely define the condition. Embodiment 5 can be any such high dimensional data that requires classification. The multilayer PCA Classifier can be executed on this data using available truth data, fingerprint features can be selected and used for further classification. Imaging data of cancerous tissues and cells can be processed using the multilayer PCA classifier to identify abnormalities in the tissues that will enable the identification of the cancer or disease if present.

Although the present invention implements a classifier that can classify human biological samples as disease or healthy, it can also be used to classify objects belonging to two different classes that are linearly separable. The invention can be used on any such data where a classification between two separate classes is required. Such fields of technology could include but not be limited to image processing, signal communications, binary data, other biological data and similar forms of data. The invention claims a generalized process that can perform classification on any linearly separable data or signals belonging to different classes, by analyzing the statistical as well as inherent property of the information. In those signal or data types where the data are not linearly separable, a linearization process can be applied to transform the data, and the present invention will still be able to be implemented using the multilayer PCA Classifier, without affecting the working of the invention. The multilayer PCA code can be used as a remote (offline) process for analyzing the data as well.

What is claimed is:

1. A method of diagnosing disease in a patient's biological sample using a computer-implemented multilayer Principal Component Analysis (PCA) Classifier comprising:
    obtaining gene expression profile data, comprising gene expression values of human biological samples with known disease/disease stages and control/healthy characteristics, also known as true positives/controls patient biological samples;
    preprocessing the gene expression profile data;
    generating using the preprocessed gene expression profile data, training samples comprising a fraction of the true positives/controls patient biological samples, and test/validation samples comprising another fraction of the true positives/controls patient biological samples;
    generating using the preprocessed gene expression profile data, a training set comprising a matrix of genes by training samples;
    performing a t-test on the training set, and generating a new training set comprising a matrix of genes by training samples as input to a first PCA layer;
    selecting, using the first PCA layer, genes to add to a Gene Pool A by performing a linear transformation on the new training set to generate a matrix of gene scores, wherein genes with an absolute value gene score above a variable threshold between 60% to 85% of a maximum gene score in the matrix of gene scores are added to Gene Pool A;
    generating, using a transpose of the new training set, a matrix of training samples by genes, as input to a second PCA layer;
    selecting, using the second PCA layer, genes to add to a Gene Pool B by performing a linear transformation on the transpose of the new training set, to generate first principal component vectors comprising coefficients of linear combinations of the genes, wherein genes with absolute value coefficients greater than $1/(sqrt(total$ number of gene coefficients in leading principal component vectors)) are added to Gene Pool B;
    identifying disease specific fingerprint genes by determining genes common to Gene Pool A and Gene Pool B;
    generating, using the disease specific fingerprint genes, a matrix of disease specific fingerprint genes by training samples;
    classifying, using a third PCA layer, expression levels of the disease specific fingerprint genes by performing a linear transformation on the matrix of fingerprint genes by training samples, to generate a matrix of gene scores, to identify fingerprint genes with positive valued gene scores as upregulated, and to identify fingerprint genes with negative valued gene scores as downregulated;
    identifying, using the expression values of the upregulated or downregulated disease specific fingerprint genes, treatment plans and medications to treat the specific disease;
    generating, using the disease specific fingerprint genes and the test/validation samples, a matrix of disease specific fingerprint genes by test/validation samples;
    identifying, using a fourth PCA layer, the test/validation samples as disease or healthy, by performing linear transformation on a matrix of test/validation samples by disease specific fingerprint genes, to create principal component vectors, wherein two largest variance principal component vectors are selected and multiplied with the matrix of the disease specific fingerprint genes by test/validation samples, to create a graphical plot on a computer display screen to distinguish the disease test/validation samples from healthy test/validation samples, wherein the test/validation samples are classified as disease/healthy with a certain set accuracy;
    generating, using the four PCA layers, disease specific fingerprint genes for a plurality of diseases;
    generating using the four PCA layers, a plurality of matrices comprising gene expression profile data of disease specific fingerprint genes by disease specific true positive patient biological samples for the plurality of diseases;
    generating a fingerprint gene data matrix comprising the plurality of matrices of gene expression profile data of disease specific fingerprint genes by disease specific true positive patient biological samples, and a fingerprint gene library comprising the disease specific fingerprint genes for the plurality of diseases;
    generating a fingerprint gene database comprising the fingerprint gene data matrix and the fingerprint gene library for identifying disease in patients, and administering medications;
    obtaining a test patient's biological sample from comprising gene expression profile data of the test patient's biological sample, using an invasive procedure;
    generating using each matrix of gene expression profile data of disease specific fingerprint genes by disease specific true positive patient biological samples from the fingerprint gene data matrix and the test patient's gene expression profile data, a plurality of matrices to screen the test patient's biological sample for disease using the plurality of matrices thus generated, wherein each matrix in the plurality of matrices screens the test patient's biological sample for a specific disease;
    identifying, using the fourth PCA layer, presence of a specific disease in the test patient's biological sample, by performing linear transformation on each matrix in the plurality of matrices of gene expression profile data of disease specific fingerprint genes by disease specific true positive patient biological samples, to create principal component vectors, wherein two largest variance principal component vectors are selected to create graphical plots on a computer display screen that classifies the test patient's biological sample as disease or healthy;
    administering, using the expression values of the upregulated or downregulated disease specific fingerprint genes, treatment plans and medications to treat the specific disease in the test patient's biological sample.

2. The method of claim 1 wherein generating the matrix of of genes by training samples as input to the first PCA layer comprises:
   obtaining the gene expression profile data from the National Center for Biotechnology Information Gene Expression Omnibus for the plurality of diseases and disease stages;
   preprocessing the gene expression profile data by normalizing gene expression values across samples, filtering out genes with low expression values and low variance across samples;
   generating using the preprocessed gene expression profile data, the training samples comprising two-thirds of samples in the true positives/controls patient biological samples, and the test/validation samples comprising one-third of samples in the true positives/controls patient biological samples;
   performing the t-test on the training set, to eliminate genes with p-value<0.00001.

3. The method of claim 1 wherein identifying the presence of a specific disease in the test patient's biological sample comprises:
   generating the disease specific fingerprint genes for the plurality of diseases using the four PCA layers, wherein the plurality of diseases also comprises multiple stages of the diseases;
   generating the fingerprint gene library comprising the disease specific fingerprint genes for the plurality of diseases;
   generating the fingerprint gene data matrix comprising the plurality of matrices of gene expression profile data of disease specific fingerprint genes by disease specific true positive patient biological samples, for the plurality of diseases;
   obtaining the test patient's biological sample using an invasive procedure;
   generating the test patient's gene expression profile data; and
   testing for presence of disease in the test patient's biological sample, by using the fourth PCA layer on each individual matrix of gene expression profile data of disease specific fingerprint genes by disease specific true positive patient biological samples, from the plurality of matrices of gene expression profile data of disease specific fingerprint genes by disease specific true positive patient biological samples from the fingerprint gene data matrix, to create graphical plots on a computer display screen that classifies the test patient's biological sample as disease or healthy.

4. The method of claim 1 wherein identifying the presence of a specific disease in the test patient's biological sample further comprises:
   obtaining the test patient's biological sample using an invasive procedure, wherein the types of biological samples comprise blood or tissues;
   extracting the test patient's gene expression profile data from the test patient's biological sample using microarray technology in a laboratory, and normalizing the test patient's gene expression profile data;
   generating a new matrix of gene expression profile data of disease specific fingerprint genes by disease specific true positive patient biological samples from the fingerprint gene data matrix to also include the test patient's gene expression profile data in the new matrix, to identify using the fourth PCA layer, presence of the specific disease in the test patient's biological sample;
   generating, using the fourth PCA layer, principal component vectors by performing linear transformation on the new matrix of gene expression profile data wherein two largest variance principal component vectors are selected to create graphical plots on a computer display screen that classifies the test patient's biological sample as disease or healthy;
   identifying presence of a specific disease if any, from the location of the test patient's biological sample in the graphical plot on the computer display screen, wherein the location of the test patient's biological sample amongst the disease specific true positive samples in the graphical display plot indicates the presence of the same disease as that of the disease specific true positive samples, while the location of the test patient's biological sample distanced from the disease specific true positive samples in the graphical display plot determines that the test patient's biological sample does not have the same disease as the disease specific true positive samples.

5. The method of claim 4 wherein identifying presence of a specific disease in the test patient's biological sample further comprises:
   generating a plurality of the new matrices of gene expression profile data of disease specific fingerprint genes by disease specific true positive patient biological samples from the fingerprint gene data matrix to also include the test patient's gene expression profile data in the new matrix, using each individual matrix of gene expression profile data of disease specific fingerprint genes by disease specific true positive patient biological samples, from the plurality of matrices of gene expression profile data of disease specific fingerprint genes by disease specific true positive patient biological samples, in the fingerprint gene data matrix to identify using the fourth PCA layer, presence of other diseases in the test patient's biological sample;
   identifying, using the fourth PCA layer, presence of other diseases if any, in the test patient's biological sample, by performing linear transformation on each individual new matrix in the plurality of new matrices, to create principal component vectors, wherein two largest variance principal component vectors are selected to create graphical plots on a computer display screen that classifies the test patient's biological sample as disease or healthy.

6. The method of claim 1 further comprising:
   classifying, using the third PCA layer, expression levels of the disease specific fingerprint genes as upregulated or downregulated, for each disease in the plurality of diseases;
   generating, using the expression values of the upregulated or downregulated disease specific fingerprint genes, treatment plans and medications to precisely target the specific disease in the test patient's biological sample, wherein the expression levels of the fingerprint genes in the test patient's biological sample enables the administering of personalized medicine to the test patient.

* * * * *